United States Patent
Matsuura et al.

(10) Patent No.: US 10,478,146 B2
(45) Date of Patent: Nov. 19, 2019

(54) RADIATION IRRADIATION DEVICE

(71) Applicant: FUJIFILM Corporation, Tokyo (JP)

(72) Inventors: Masayoshi Matsuura, Kanagawa (JP); Naoaki Hagiwara, Kanagawa (JP); Takeyasu Kobayashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 214 days.

(21) Appl. No.: 15/623,391

(22) Filed: Jun. 15, 2017

(65) Prior Publication Data

US 2018/0000443 A1 Jan. 4, 2018

(30) Foreign Application Priority Data

Jul. 1, 2016 (JP) ................................. 2016-131363

(51) Int. Cl.
*H05G 1/10* (2006.01)
*A61B 6/00* (2006.01)

(52) U.S. Cl.
CPC .............. *A61B 6/56* (2013.01); *A61B 6/4283* (2013.01); *A61B 6/4405* (2013.01); *A61B 6/587* (2013.01)

(58) Field of Classification Search
CPC ....... A61B 6/56; A61B 6/4283; A61B 6/4405; A61B 6/587
See application file for complete search history.

(56) References Cited

U.S. PATENT DOCUMENTS

| | | | | |
|---|---|---|---|---|
| 2006/0070384 | A1* | 4/2006 | Ertel | G01T 1/2018 62/3.3 |
| 2010/0220837 | A1* | 9/2010 | Bressel | A61B 6/032 378/98 |
| 2012/0027177 | A1* | 2/2012 | Ogata | H01J 35/065 378/95 |
| 2013/0230142 | A1 | 9/2013 | Murata et al. | |
| 2015/0023468 | A1* | 1/2015 | Zou | A61B 6/4405 378/62 |

FOREIGN PATENT DOCUMENTS

| | | |
|---|---|---|
| JP | 2010-273827 | 12/2010 |
| JP | 2013-180059 | 9/2013 |
| JP | 2014-150948 | 8/2014 |
| JP | 2015100377 | 6/2015 |
| JP | 2015119775 | 7/2015 |
| JP | 2015198840 | 11/2015 |
| KR | 20020062453 A * | 7/2002 |

OTHER PUBLICATIONS

"Office Action of Japan Counterpart Application," dated Jul. 23, 2019, with English translation thereof, pp. 1-6.

* cited by examiner

*Primary Examiner* — Kiho Kim
(74) *Attorney, Agent, or Firm* — JCIPRNET

(57) ABSTRACT

A radiation irradiation device includes a radiation generating part that generates radiation; an arm part having the radiation generating part attached to one end thereof; a main body part having the other end of the arm part connected thereto; an electric power supply part provided at the main body part; and a cable part for electrically connecting the power supply part and the radiation part. The electric power supply part has a battery part having lithium ion batteries connected in parallel, and a first booster circuit part that boosts a voltage output from the battery part. The radiation generating part has a second booster circuit part that further boosts a voltage that is boosted by the first booster circuit part and is input to the radiation generating part via the cable part which is extended along the arm part.

20 Claims, 7 Drawing Sheets

RADIATION IRRADIATION DEVICE

CROSS-REFERENCE TO RELATED APPLICATIONS

The present application claims priority under 35 U.S.C. § 119 to Japanese Patent Application No. 2016-131363, filed on Jul. 1, 2016. Each of the above application(s) is hereby expressly incorporated by reference, in its entirety, into the present application.

BACKGROUND OF THE INVENTION

1. Field of the Invention

The present invention relates to a radiation irradiation device having an arm part provided with a radiation source.

2. Description of the Related Art

In the related art, portable radiation irradiation devices used in a case where a patient's radiation image are captured in operating rooms, examination rooms, or inpatient rooms have been suggested variously (refer to JP2013-180059A, JP2010-273827A, and JP2014-150948A).

The portable radiation irradiation devices basically include a leg part enabled to travel by wheels, a main body part that houses a control part consisting of a battery for driving a radiation source, an electric circuit related to the driving of the radiation source, and the like and is held on the leg part, and an arm part connected to the main body part, and are configured by attaching the radiation source to a tip of the arm part.

When such radiation irradiation devices are used, a radiation irradiation device is first moved to the vicinity of a patient's bed. Next, the radiation source is moved to a desired position, and a radiation detector is moved to a desired position behind a subject. Then, in this state, the subject is irradiated with radiation by driving the radiation source, and a radiation image of the subject is acquired by detecting the radiation transmitted through the subject using the radiation detector.

Here, in the related art, in the portable radiation irradiation devices, lead storage batteries are used as batteries. However, in a case where the lead batteries are frequently charged, degradation of the batteries becomes early due to a memory effect, and energy density is small. Therefore, there are problems in that the weight becomes heavy.

Thus, it is suggested that lithium ion batteries are used as the batteries of the radiation irradiation devices (for example, refer to JP2013-180059A, JP2010-273827A, and JP2014-150948A).

SUMMARY OF THE INVENTION

However, even in a case where the lithium ion batteries are used, there are several problems. The lithium ion batteries have large internal resistance because the lithium ion batteries are connected in series. Hence, in a case where a high current is sent through a radiation source when generating radiation, a voltage drop of the lithium ion batteries become large, and becomes equal to or lower than a lower limit of battery rating. As a result, the lifespan of the lithium ion batteries becomes short.

Additionally, if the number of lithium ion batteries is increased by connecting the lithium ion batteries more in series, the value of a current of each lithium ion battery can be held down. However, due to the serialization, internal resistance becomes large, and the voltage drop increases. Moreover, in a case where a voltage that exceeds 60 V is made to output by connecting the lithium ion batteries in series, there is a problem an insulation creepage space distance becomes large and the size increases.

Additionally, in a case where a voltage of 60 V or less is made to output from the lithium ion batteries, it is necessary to boost the output voltage to supply the boosted voltage to the radiation source.

However, in the case of the above-described portable radiation irradiation devices, it is necessary to supply the voltage output from the batteries of the main body part to the radiation source via the arm part. In this case, in the main body part, in order to perform boosting up to a service voltage (for example, about 100 kV) of the radiation source, it is necessary to provide a high-voltage cable within the arm part. However, since the high-voltage cable is expensive, cost increases. Moreover, since the high-voltage cable is covered with a thick insulating member, the degree of freedom of movement of the arm part is impaired by this high-voltage cable being extended inside the arm part.

Thus, it is also considered that boosting is performed not in the main body part but on the radiation source side. In this case, since the value of a voltage that goes via the arm part becomes small. Therefore, there is a problem in that influence is likely to be received by the noise from the outside.

In view of the above problem, an object of the invention is to provide a radiation irradiation device that can further improve noise resistance and the degree of freedom of an arm part without causing the increase in cost as described above.

A radiation irradiation device of the invention includes a radiation generating part that generates radiation; an arm part having the radiation generating part attached to one end thereof; a main body part having the other end of the arm part connected thereto; an electric power supply part provided at the main body part; and a cable part for electrically connecting the power supply part and the radiation part. The electric power supply part has a battery part having lithium ion batteries connected in parallel, and a first booster circuit part that boosts a voltage output from the battery part. The radiation generating part has a second booster circuit part that further boosts a voltage that is boosted by the first booster circuit part and is input to the radiation generating part via the cable part which is extended along the arm part.

Additionally, in the radiation irradiation device of the above invention, the first booster circuit part can boost the voltage output from the battery part to a voltage of 4 times or more and 6 times or less.

Additionally, in the radiation irradiation device of the above invention, the second booster circuit part can boost the voltage input via the arm part to a voltage of 50 times or more.

Additionally, in the radiation irradiation device of the invention, it is preferable that a voltage output from the first booster circuit part is 60 V or more and 300 V or less.

Additionally, in the radiation irradiation device of the above invention, it is preferable that the same poles of the lithium ion batteries are short-circuited to each other.

Additionally, the radiation irradiation device of the above invention can further include a cutoff part that cuts off electric power supply from the battery part to the radiation generating part.

Additionally, in the radiation irradiation device of the above invention, the cutoff part can have a cutoff circuit provided in each of the lithium ion batteries of the battery part.

Additionally, the radiation irradiation device of the above invention can further include an operating part capable of simultaneously operating a plurality of the cutoff circuits.

Additionally, in the radiation irradiation device of the above invention, it is preferable that the same poles of the lithium ion batteries are short-circuited to each other, and the cutoff part is provided in the short-circuited part.

Additionally, in the radiation irradiation device of the invention, it is preferable that the voltage output from the battery part is 60 V or less.

Additionally, in the radiation irradiation device of the invention, it is preferable that the battery part is capable of charging a radiation detector that detects the radiation transmitted through a subject.

Additionally, in the radiation irradiation device of the invention, it is preferable that the battery part is capable of supplying electric power to an external instrument.

According to the radiation irradiation device of the invention, the main body part is provided with the battery part having the lithium ion batteries connected in parallel, and the first booster circuit part that boosts the voltage output from the battery part. Thus, the first booster circuit part can perform boosting up to the magnitude of a voltage that is strong against noise. Also, the radiation generating part is provided with the second booster circuit part that further boosts the voltage input via the arm part, that is, boosting is performed on both the main body part and the radiation generating part. Thus, a voltage passing through the arm part can be made low. Hence, since it is not necessary to provide a high-voltage cable within the arm part, reduction of cost can be achieved, and the degree of freedom of the arm part can be improved.

DESCRIPTION OF THE PREFERRED EMBODIMENTS

Figure 1:
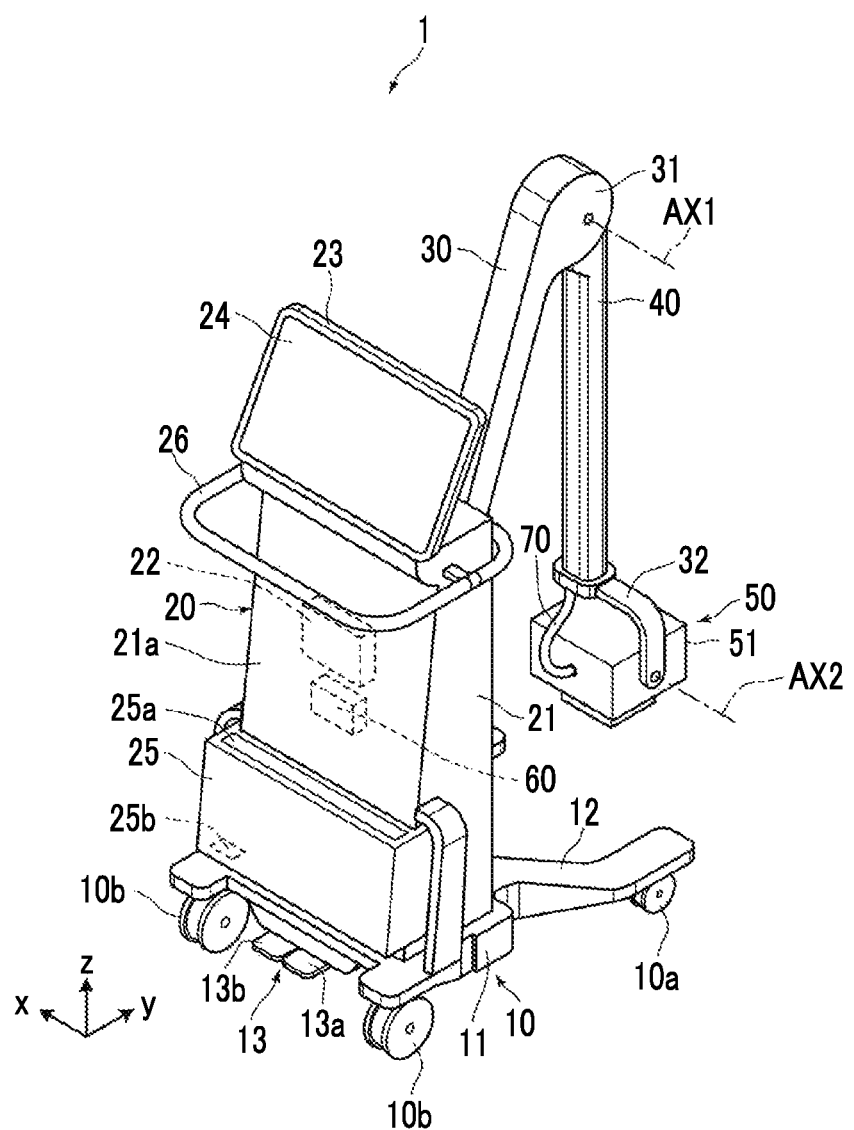
FIG. 1 is a perspective view illustrating an entire shape of a radiation irradiation device of an embodiment of the invention.
Figure 2:
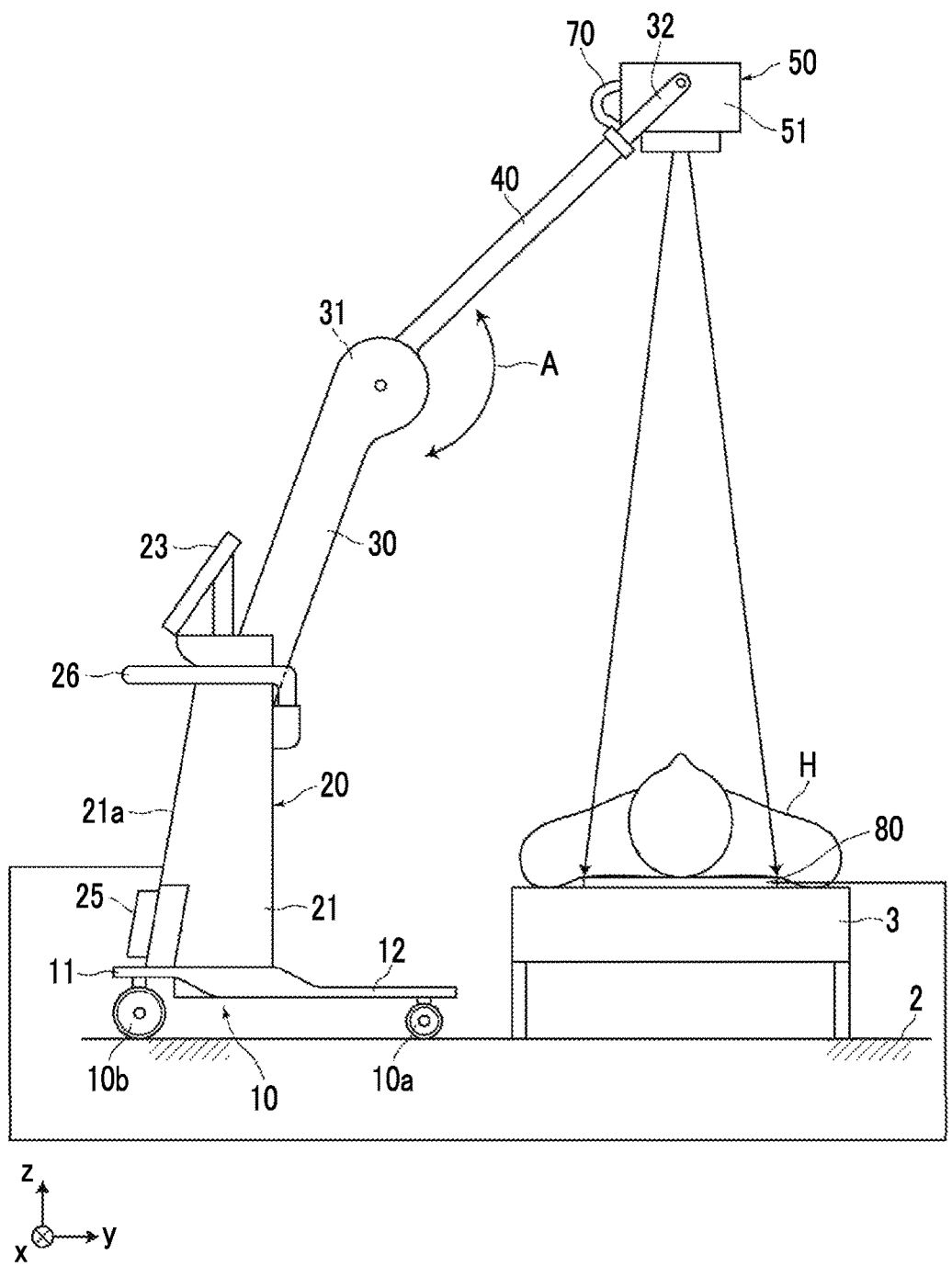
FIG. 2 is a view illustrating the state when the radiation irradiation device of the embodiment of the invention is used.

Hereinafter, a radiation irradiation device of an embodiment of the invention will be described in detail, referring to the drawings. Although the invention has features in the configuration of electric power supply to the radiation generating part in the radiation irradiation device, the entire configuration of the radiation irradiation device will first be described. FIG. 1 is a perspective view illustrating the entire shape of the radiation irradiation device of the present embodiment when being not used, and FIG. 2 is a side view illustrating the state when the radiation irradiation device of the present embodiment is used. In addition, in the following, an upper side and a lower side in the vertical direction in a state where the radiation irradiation device is placed on, for example, a device placement surface, such as a floor of a medical institution, are referred to as "up" and "down", respectively, and a direction perpendicular to the vertical direction in the same state is referred to as a "horizontal" direction. Additionally, in the views to be described below, the vertical direction is defined as a z direction, a leftward-rightward direction of the radiation irradiation device is defined as an x direction, and a forward-backward direction of the radiation irradiation device is defined as a y direction. In addition, the front herein means a side to which an arm part extends from a main body part of the radiation irradiation device when the device is used.

As illustrated in FIGS. 1 and 2, a radiation irradiation device 1 of the present embodiment includes a leg part 10, a main body part 20, a supporting member 30, an arm part 40, and a radiation generating part 50.

Figure 3:
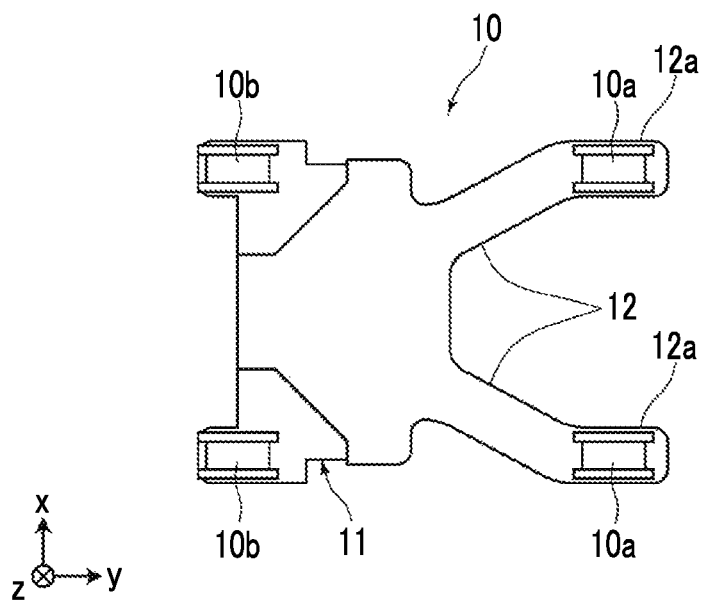
FIG. 3 is a view of a leg part as seen from below.

The leg part 10 is capable of traveling on a device placement surface 2, and consists of a plate-shaped pedestal part 11 on which the main body part 20 is placed, and a foot arm part 12 that extends from the pedestal part 11 toward the front. FIG. 3 is a view of the leg part 10 as seen from below. As illustrated in FIG. 3, the foot arm part 12 is framed in a V shape that widens in the leftward-rightward direction toward the front. First casters 10a are respectively provided on bottom surfaces of two tip parts 12a at the front of the foot arm part 12, and second casters 10b are respectively provided on bottom surfaces of two corners at the rear of the pedestal part 11. By forming the foot arm part 12 in a V shape as described above, for example, as compared to a case where the entire leg part 10 is formed in a rectangular shape, an edge part of the leg part does not easily collide against its surrounding obstacle when the leg part 10 is rotated. Thus, handling can be made easy. Additionally, weight reduction can also be achieved.

Each first caster 10a has a shaft that extends in the upward-downward direction, and is attached to the foot arm part 12 such that a rotating shaft of a wheel is revolvable within a horizontal plane about the shaft of the first caster. Additionally, each second caster 10b also has a shaft that extends in the upward-downward direction, and is attached to the pedestal part 11 such that a rotating shaft of a wheel is revolvable within the horizontal plane about the shaft of the second caster. In addition, the rotating shaft of each wheel herein is a rotating shaft when the wheel rotates and travels. The leg part 10 is configured so as to be capable of traveling in an arbitrary direction on the device placement surface 2 by the first casters 10a and the second casters 10b.

Additionally, as illustrated in FIG. 1, a pedal part 13 is provided at the rear of the leg part 10. The pedal part 13 consists of two pedals of a first pedal 13a and a second pedal 13b. The first pedal 13a is a pedal for bringing the second casters 10b into a non-revolvable state. As a user steps on the first pedal 13a, the second casters 10b are configured so as to be locked in revolution by a locking mechanism and brought into the non-revolvable state.

Additionally, the second pedal 13b is a pedal for bringing the second casters 10b into a revolvable state from the non-revolvable state. As the user steps on the second pedal 13b, the second casters 10b are configured so as to be released from the locking by the locking mechanism and brought into the revolvable state again.

A well-known configuration can be used as the locking mechanism that locks the revolution of the second casters 10b. For example, the revolution may be locked such that both sides of the wheels of the second casters 10b are sandwiched by plate-shaped members, or the revolution may be locked by providing members that stop the rotation of shafts of the second caster 10b that extend in the upward-downward direction.

The main body part 20 is placed on the pedestal part 11 of the leg part 10, and includes a housing 21. A control part 22 that controls driving of the radiation irradiation device 1 and an electric power supply part 60 are housed within the housing 21.

The control part 22 performs control regarding generation and irradiation of radiation, such as a tube current, irradiation time, and a tube voltage, in the radiation generating part 50, and control regarding acquisition of radiation images, such as image processing of a radiation image acquired by the radiation detector to be described below. The control part 22 is configured of, for example, a computer in which a program for control is installed, exclusive hardware, or combination of both.

The electric power supply part 60 supplies electric power to the radiation generating part 50, a monitor 23, and the radiation detector housed within a cradle 25 to be described below. In addition, the monitor 23 may be configured so as to be attachable to and detachable from the main body part 20. In that case, the electric power supply part 60 supplies electric power to a battery built in the monitor 23 to charge the battery. Additionally, the radiation detector also has a battery built therein, and the electric power supply part 60 supplies electric power to the built-in battery to charge the battery.

Figure 4:
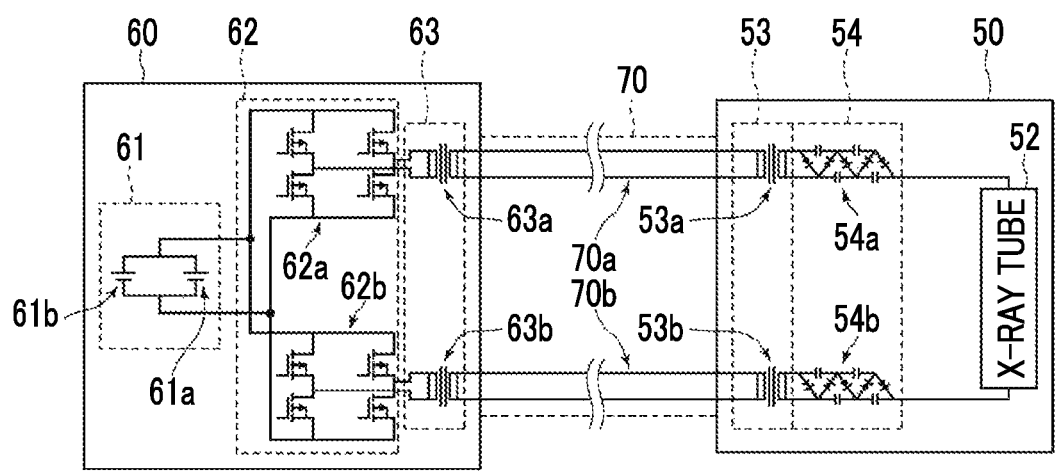
FIG. 4 is a schematic view illustrating an electrical configuration of an electric power supply part and a radiation generating part.

FIG. 4 is a schematic view illustrating an electrical configuration of the electric power supply part 60 and the radiation generating part 50. As illustrated in FIG. 4, the electric power supply part 60 includes a battery part 61, an inverter circuit part 62, and a first booster circuit part 63.

The battery part 61 has a plurality of lithium ion batteries connected in parallel. Specifically, the battery part 61 of the present embodiment has two lithium ion batteries 61a, 61b connected in parallel. In addition, in the present embodiment, although the two lithium ion batteries are connected in parallel, the number of lithium ion batteries is not limited to two, and three or more lithium ion batteries may be connected in parallel.

Additionally, it is preferable that the plurality of lithium ion batteries are short-circuited between the same poles. By connecting the lithium ion batteries in this way, since a path through which a large current flows can be limited to a small extent, noise can be reduced.

By connecting the lithium ion batteries in this way, as compared to a case where lithium ion batteries are connected in series, internal resistance can be made small. Accordingly, a voltage drop at the time of generation of radiation can be suppressed, and lifespan degradation of the lithium ion batteries can be suppressed. As compared to the case where the lithium ion batteries are connected in series, an insulation creepage space distance can be made small, and size reduction can be achieved.

The lithium ion batteries 61a, 61b are a cell formed by connecting a plurality of lithium ion batteries in parallel, and output voltages of 48 V, respectively. Although the voltage output from each of the lithium ion batteries 61a, 61b is not limited to 48 V, it is desirable that this voltage is 60 V or less. By setting the voltage to 60 V or less, the insulation creepage space distance can be made small, and size reduction can be achieved.

The inverter circuit part 62 converts a direct current voltage output from the battery part 61 into an alternating voltage. Specifically, the inverter circuit part 62 includes a positive electrode side inverter circuit 62a and a negative electrode side inverter circuit 62b. In addition, the circuit configuration of the inverter circuits is not limited to the circuit configuration illustrated in FIG. 4, and other well-known inverter circuits may be adopted.

The first booster circuit part 63 boosts an alternating voltage output from the inverter circuit part 62. Specifically, the first booster circuit part 63 includes a positive electrode side first booster circuit 63a and the negative electrode side first booster circuit 63b. The positive electrode side first booster circuit 63a of the present embodiment boosts a positive alternating voltage output from the positive electrode side inverter circuit 62a, and boosts the positive alternating voltage to, for example, an alternating voltage of 4 times or more and 6 times or less. In the present embodiment, the positive electrode side first booster circuit 63a boosts an alternating voltage of 48 V output from the positive electrode side inverter circuit 62a to an alternating voltage of 250 V.

By boosting the positive alternating voltage to the alternating voltage of 4 times or more using the positive electrode side first booster circuit 63a in this way, resistance against the noise from the outside can be made strong. Additionally, by boosting the positive alternating voltage to the alternating voltage of 6 times or less using the positive electrode side first booster circuit 63a, it is not necessary to use a high-voltage cable as a cable part 70 to be described below, and reduction of cost can be achieved. Moreover, since wiring line coating of the cable part 70 can be made thin, the degree of freedom of the cable part 70 can be improved. Accordingly, the movement of the arm part 40 (to be described below) in which the cable part 70 extends can be made smooth. Specifically, it is desirable that the alternating voltage output from the positive electrode side first booster circuit 63a, is 60 V or more and 300 V or less.

Meanwhile, the negative electrode side first booster circuit 63b boosts a negative alternating voltage output from the negative electrode side inverter circuit 62b, and boosts the negative alternating voltage to, for example, an alternating voltage of 4 times or more and 6 times or less, similar to the positive electrode side first booster circuit 63a. In the present embodiment, the negative electrode side first booster circuit 63b boosts an alternating voltage of −48 V output from the negative electrode side inverter circuit 62b to an alternating voltage of −250 V. It is desirable that the alternating voltage output from the negative electrode side first booster circuit 63b is −300 V or more and −60 V or less. In addition, various well-known circuit configurations can be adopted as specific circuit configurations of the first booster circuit part 63.

In addition, the electric power supply part 60 is connected to an external power source via a connector (not illustrated), and receives the supply of electric power from the external power source, and thereby, the lithium ion batteries 61a, 61b are charged.

The alternating voltage output from the electric power supply part 60 is supplied to the radiation generating part 50 via the cable part 70. The cable part 70 electrically connects the electric power supply part 60 provided within the main body part 20 and the radiation generating part 50 provided at the tip of the arm part 40 to each other, and includes a positive electrode side electric power supply wiring line 70a and a negative electrode side electric power supply wiring line 70b. Each of the positive electrode side electric power supply wiring line 70a and the negative electrode side electric power supply wiring line 70b is formed by covering a conductive member with an insulating member, and extends inside the supporting member 30 and inside the arm part 40. The length of the cable part 70 is, for example, about 3 m and the wiring resistance of the cable part is, for example, about 75 mΩ. Additionally, although not illustrated, the cable part 70 includes a control signal wiring line that supplies a control signal output from the control part 22 to the radiation generating part 50, in addition to the positive electrode side electric power supply wiring line 70a and the negative electrode side electric power supply wiring line 70b.

The radiation generating part 50 is a so-called mono-tank in which a radiation source, a booster circuit, a voltage doubler rectifier circuit, and the like are provided within the housing 51 (refer to FIG. 1). As illustrated in FIG. 4, the radiation generating part 50 of the present embodiment includes an X-ray tube 52 serving as a radiation source, a second booster circuit part 53, and a voltage doubler rectifier circuit part 54.

The second booster circuit part 53 boosts an alternating voltage input via the cable part 70. Specifically, the second booster circuit part 53 includes a positive electrode side second booster circuit 53a, and a negative electrode side second booster circuit 53b. The positive electrode side second booster circuit 53a of the present embodiment boosts the positive alternating voltage supplied from the positive electrode side electric power supply wiring line 70a, and boosts the positive alternating voltage to, for example, an alternating voltage of 50 times or more. The positive electrode side second booster circuit 53a of the present embodiment boosts the positive alternating voltage of 250 V supplied from the positive electrode side electric power supply wiring line 70a, and boosts the positive alternating voltage to an alternating voltage of 12.5 kV.

Meanwhile, the negative electrode side second booster circuit 53b boosts the negative alternating voltage supplied from the negative electrode side electric power supply wiring line 70b, and boosts the negative alternating voltage to, for example, an alternating voltage of 50 times or more, similar to the positive electrode side second booster circuit 53a. The negative electrode side second booster circuit 53b of the present embodiment boosts the alternating voltage of −250 V supplied from the negative electrode side electric power supply wiring line 70b to an alternating voltage of −12.5 kV. In addition, various well-known circuit configurations can be adopted as specific circuit configurations of the second booster circuit part 53.

The voltage doubler rectifier circuit part 54 doubles and rectifies an alternating voltage output from the second booster circuit part 53. Specifically, the voltage doubler rectifier circuit part 54 includes a positive electrode side voltage doubler rectifier circuit 54a and a negative electrode side voltage doubler rectifier circuit 54b. The positive electrode side voltage doubler rectifier circuit 54a doubles and rectifies the positive alternating voltage output from the positive electrode side second booster circuit 53a, and rectifies the alternating voltage to, for example, a positive direct current voltage of 4 times. The positive electrode side voltage doubler rectifier circuit 54a of the present embodiment rectifies the alternating voltage of 12.5 kV boosted by the positive electrode side second booster circuit 53a to a direct current voltage of 50 kV.

Meanwhile, the negative electrode side voltage doubler rectifier circuit 54b doubles and rectifies the negative alternating voltage output from the negative electrode side second booster circuit 53b, and rectifies the negative alternating current to, for example, a negative direct current voltage of 4 times, similar to the positive electrode side voltage doubler rectifier circuit 54a. The negative electrode side voltage doubler rectifier circuit 54b of the present embodiment rectifies the alternating voltage of 12.5 kV boosted by the negative electrode side second booster circuit 53b to a direct current voltage of −50 kV. In addition, the specific circuit configuration of the voltage doubler rectifier circuit part 54 is not limited to the circuit configuration illustrated in FIG. 4, and various well-known circuit configurations can be adopted.

The X-ray tube 52 generates radiation by applying a direct current voltage output from the voltage doubler rectifier circuit part 54. In the present embodiment, as described above, the direct current voltage of 50 kV is supplied to a positive electrode side of the X-ray tube 52 by the positive electrode side voltage doubler rectifier circuit 54a, and the direct current voltage of −50 kV is supplied to a negative electrode side of the X-ray tube 52 by the negative electrode side voltage doubler rectifier circuit 54b. As a result, the direct current voltage of 100 kV is applied to the X-ray tube 52.

Emission of the radiation from the X-ray tube 52 of the radiation generating part 50 is performed by an operator's instruction from an input part 24 in the monitor 23.

Returning to FIGS. 1 and 2, an L-shaped radiation source attachment part 32 is provided at a tip (one end) of the arm part 40. The radiation generating part 50 is attached to the one end of the arm part 40 via the radiation source attachment part 32. As illustrated in FIGS. 1 and 2, the cable part 70 taken out from the one end of the arm part 40 is connected to the radiation generating part 50 via a connector.

The radiation generating part 50 is connected to the radiation source attachment part 32 so as to be rotationally movable with an axis AX2 as a rotational movement axis. The rotational movement axis AX2 is an axis that extends in the leftward-rightward direction (x direction). In addition, the radiation source attachment part 32 holds the radiation generating part 50 such that the radiation generating part 50 moves rotationally via a friction mechanism. For this reason, the radiation generating part 50 is rotationally movable by applying a certain degree of strong external force, does not move rotationally unless an external force is applied, and maintains a relative angle with respect to the arm part 40.

Figure 5:
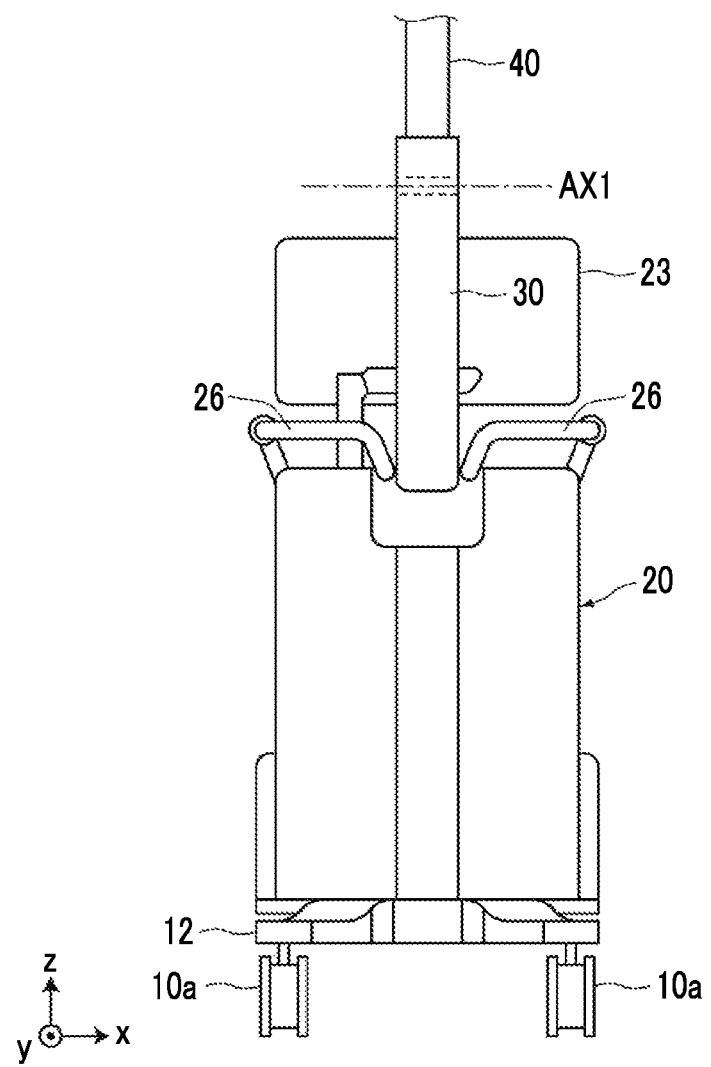
FIG. 5 is a view of the radiation irradiation device illustrated in FIG. 1 as seen from the front.

Additionally, the monitor 23 is attached to an upper surface of the housing 21. Additionally, a handle part 26 for pushing or pulling the radiation irradiation device 1 is attached to an upper part of the housing 21. The handle part 26 is provided so as to go around the housing 21, and is configured so as to be capable of being held not only from a rear side of the radiation irradiation device 1 but also from a front side or a lateral side. FIG. 5 is a view of the radiation irradiation device 1 as seen from the front. As illustrated in FIG. 5, the handle part 26 is provided so as to go around to a front side of the main body part 20.

The monitor 23 consists of a liquid crystal panel or the like, and displays a radiation image acquired by imaging of a subject, and various kinds of information required for the control of the radiation irradiation device 1. Additionally, the monitor 23 includes the touch panel type input part 24, and receives input of various instructions required for the operation of the radiation irradiation device 1. Specifically, input for setting of imaging conditions and input for imaging, that is, emission of radiation, is received. The monitor 23 is attached to the upper surface of the housing 21 so as to be capable of changing the inclination and the rotational position of a display surface with respect to the horizontal direction. Additionally, instead of the touch panel type input part 24, buttons for performing various operations may be included as the input part.

Additionally, a tablet computer may be used as the monitor 23. In this case, the electric power supply part 60 supplies electric power to the tablet computer with or without wires to charge the tablet computer. Additionally, in a case where the tablet computer is used as the monitor 23, the above-described control part 22 may be built in the tablet computer.

One end of the supporting member 30 is connected to the other end of the arm part 40. The arm part 40 is connected to the supporting member 30 so as to be rotationally movable with an axis AX1 as a rotational movement axis. The rotational movement axis AX1 is an axis that extends in the leftward-rightward direction (x direction). The arm part 40 moves rotationally in a direction of arrow A illustrated in FIG. 2 such that an angle followed with the supporting member 30 is changed about the rotational movement axis AX1.

A rotational movement part 31 having the rotational movement axis AX1 holds the arm part 40 such that the arm part 40 moves rotationally via the friction mechanism. For this reason, the arm part 40 is rotationally movable by applying a certain degree of strong external force, does not move rotationally unless an external force is applied, and maintains a relative angle with respect to the supporting member 30.

In addition, although the rotational movement of the arm part 40 and the radiation generating part 50 is performed via the friction mechanism, rotational movement positions of these parts may be fixed by a well-known locking mechanism. In this case, the rotational movements of the arm part 40 and the radiation generating part 50 become possible by releasing the locking mechanism. The rotational movement positions can be fixed by locking the locking mechanism at desired rotational movement positions.

The other end of the supporting member 30 is connected to the surface of the main body part 20 on the front side. The supporting member 30 is provided so as to be fixed with respect to the main body part 20, and is attached so as to be non-rotatable with respect to the main body part 20. In the present embodiment, as described above, the orientation of the arm part 40 can be freely changed together with the main body part 20 by the revolution of the first casters 10*a* and the second casters 10*b*. Thus, it is not necessary to make the supporting member 30 have a degree of freedom, and a simpler configuration can be adopted. However, the invention is not limited to this, and the supporting member 30 may be configured to rotate with emphasis on handleability. That is, the supporting member 30 may be configured so as to be rotatable with an axis passing through the center of the portion of the supporting member 30 connected to the main body part 20 and extending in the vertical direction as a rotation axis.

In the present embodiment, when a subject is imaged, as illustrated in FIG. 2, the imaging is performed by arranging a radiation detector 80 under a subject H that lies on ones' back on a bed 3 and irradiating the subject H with the radiation emitted from the radiation generating part 50. In addition, the radiation detector 80 and the radiation irradiation device 1 are connected together with or without wires. Accordingly, the radiation image of the subject H acquired by the radiation detector 80 is directly input to the radiation irradiation device 1.

Figure 6:
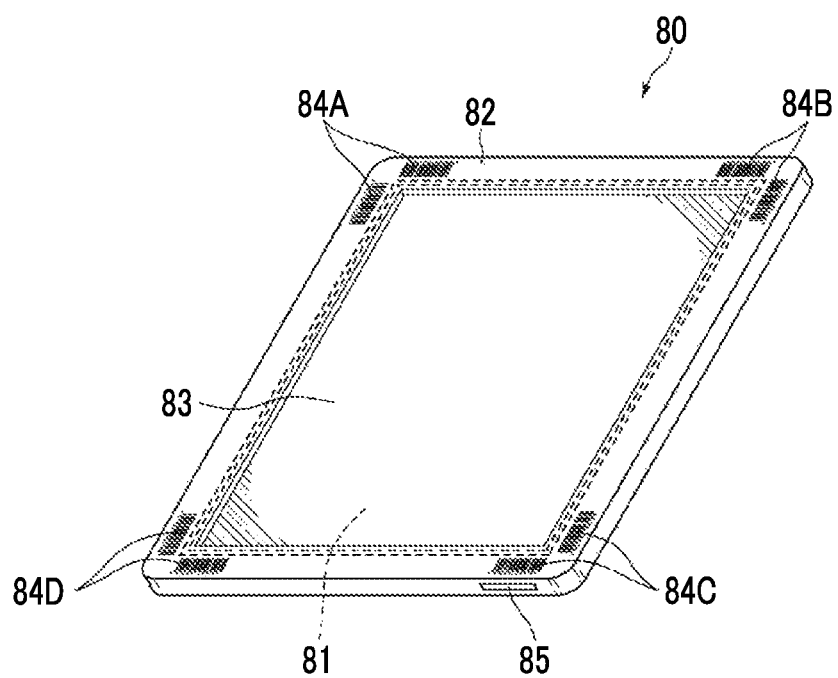
FIG. 6 is an external perspective view of a radiation detector as seen from a radiation detection surface side.

Here, a radiation detector 80 will be briefly described with reference to FIG. 6. FIG. 6 is an external perspective view of the radiation detector as seen from a front surface that is a radiation detection surface side. As illustrated in FIG. 6, the radiation detector 80 is a cassette type radiation detector including a housing 82 that has a rectangular flat plate shape and houses a detecting part 81. The detecting part 81 includes a scintillator (fluorescent body) that converts incident radiation into visible light as is well known, and a thin film transistor (TFT) active matrix substrate. A rectangular imaging region where a plurality of pixels that accumulate electrical charge according to the visible light from the scintillator are arrayed is formed on the TFT active matrix substrate.

Additionally, the housing 82 includes a round-chamfered metallic frame. A gate driver which gives a gate pulse to a gate of a TFT to switch the TFT, an imaging control part including a signal processing circuit that converts an electrical charge accumulated in a pixel into an analog electrical signal representing an X-ray image to output the converted signal, and the like in addition to the detecting part 81 are built in the housing. Additionally, the housing 82 has, for example, a size based on International Organization for Standardization (ISO) 4090:2001 that is substantially the same as a film cassette, an imaging plate (IP) cassette, and a computed radiography (CR) cassette.

A transmission plate 83 that allows radiation to be transmitted therethrough is attached to a front surface of the housing 82. The transmission plate 83 has a size that substantially coincides with a detection region of radiation in the radiation detector 80, and is formed of a carbon material that is lightweight, has high rigidity, and has high radiation transmissivity. In addition, the shape of the detection region is the same oblong shape as the shape of the front surface of the housing 82. Additionally, the portion of the frame of the housing 82 protrudes from the transmission plate 83 in a thickness direction of the radiation detector 80. For this reason, the transmission plate 83 is not easily damaged.

Markers 84A to 84D showing identification information for identifying the radiation detector 80 are applied to four corners of the front surface of the housing 82. In the present embodiment, the markers 84A to 84D consist of two bar codes that are orthogonal to each other, respectively.

Additionally, a connector 85 for charging the radiation detector 80 is attached to a side surface of the housing 82 on the markers 84C, 84D side.

When the radiation irradiation device 1 according to the present embodiment is used, the operator rotationally moves the arm part 40 around the rotational movement axis AX1 in an illustrated counterclockwise direction from an initial position of the arm part 40 illustrated in FIG. 1, and thereby the radiation generating part 50 is moved to a target position immediately above the subject H, as illustrated in FIG. 2. The radiation image of the subject H can be acquired by driving the radiation generating part 50 according to an instruction from the input part 24 to irradiate the subject H with radiation and detecting the radiation transmitted through the subject H, using the radiation detector 80, after the radiation generating part 50 is moved to the target position.

In addition, as the radiation detector 80, as described above, it is desirable to use a radiation detector in which the scintillator and the TFT active matrix substrate including light receiving elements are laminated and which receives irradiation of radiation from a TFT active matrix substrate side (a side opposite to a scintillator side). By using such a high-sensitivity radiation detector 80, a low-output radiation source can be used as the radiation generating part 50, and the weight of the radiation generating part 50 can be made light. In addition, generally, the radiation source output of the radiation generating part 50 and the weight of the radiation generating part 50 are in a proportional relation.

Since the weight of the radiation generating part 50 can be made light as described above, the total weight of the radiation irradiation device 1 can also be made light. Accordingly, by using the revolving casters as the second caster 10*b* (rear wheels) as in the radiation irradiation device 1 of the present embodiment, the revolution performance of the radiation irradiation device 1 can be improved, and handling can be markedly improved.

Next, a configuration in which the radiation detector 80 in the main body part 20 is capable of being housed will be described. As illustrated in FIGS. 1 and 2, the housing 21 of the main body part 20 has a flat surface 21*a* inclined to a supporting member 30 side, on a surface opposite to a side where the supporting member 30 is attached, and the flat surface 21*a* is provided with the cradle 25.

An insertion port 25*a* for inserting the radiation detector 80 is formed in an upper surface of the cradle 25. The insertion port 25*a* has an elongated shape of a size such that the radiation detector 80 is fitted thereto. In the present embodiment, one end part on a side having the connector 85 of the radiation detector 80 is inserted to the insertion port 25*a*. Accordingly, this one end part is supported by a bottom part of the cradle 25, and the radiation detector 80 is held by the cradle 25. In this case, a front surface of the radiation detector 80 is directed to a flat surface 21*a* side.

A connector 25*b* is attached to the bottom part of the cradle 25. The connector 25*b* is electrically connected to the connector 85 of the radiation detector 80 when the radiation detector 80 is held by the cradle 25. The connector 25*b* is electrically connected to the electric power supply part 60. Hence, when the radiation detector 80 is held by the cradle 25, the radiation detector 80 is charged by the electric power supply part 60 via the connector 85 of the radiation detector 80 and the connector 25*b* of the cradle 25.

In addition, a configuration in which the radiation detector 80 is chargeable by the electric power supply part 60 has been described in the present embodiment. As described above, a configuration in which the monitor 23 is chargeable by the electric power supply part 60 may be adopted. Moreover, a configuration in which an external connector is further provided at the main body part 20 and external instruments other than the monitor are connectable may be adopted. Also, a configuration in which electric power is supplied to an external instrument by the electric power supply part 60 via the external connector and the external instrument is chargeable may be adopted. As the external instrument, for example, there is a note-type computer used as a console, or the like.

Figure 7:
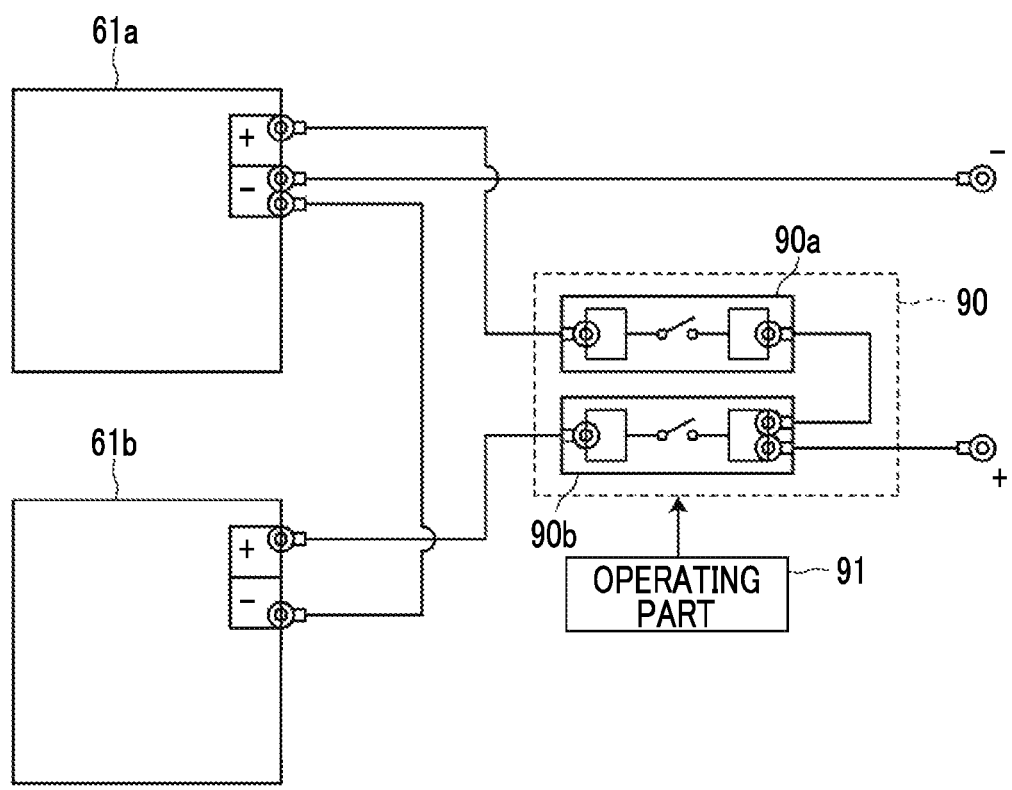
FIG. 7 is a view illustrating an example of the configuration of a cutoff part.

Additionally, in the radiation irradiation device 1 of the above embodiment, it is desirable to provide the cutoff part that cuts off the electric power supply from the battery part 61 of the electric power supply part 60 to the radiation generating part 50. By providing the cutoff part in this way, electricity can be saved by cutting off the electric power supply when being not used. Additionally, in a case where an excessive electric current flows, safety can be guaranteed by automatically cutting off the electric power supply using the cutoff part. FIG. 7 is a schematic view illustrating a specific configuration of the cutoff part 90.

As illustrated in FIG. 7, the cutoff part 90 includes a first cutoff circuit 90*a* having one end connected to a positive electrode of the lithium ion battery 61*a*, and a second cutoff circuit 90*b* having one end connected to a positive electrode of the lithium ion battery 61*b*. The other ends of the first cutoff circuit 90*a* and the second cutoff circuit 90*b* are connected to each other, and the other end of the second cutoff circuit 90*b* is connected to a positive electrode of the radiation generating part 50. Additionally, negative electrodes of the lithium ion battery 61*a* and the lithium ion battery 61*b* are short-circuited to each other, and the negative electrode on the lithium ion battery 61*a* side is connected to a negative electrode of the radiation generating part 50.

The first cutoff circuit 90*a* cuts off the electric power supply from the lithium ion battery 61*a* by being turned off, and the second cutoff circuit 90*b* cuts off the electric power supply from the lithium ion battery 61*b* by being turned off.

Figure 8:
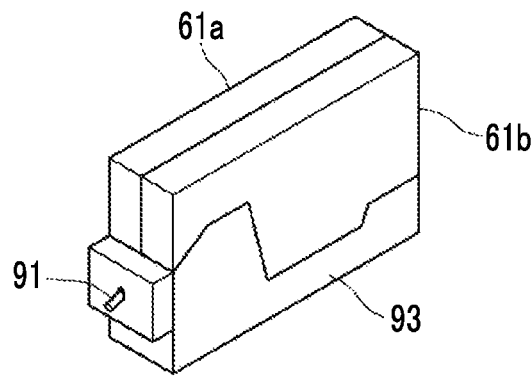
FIG. 8 is a view illustrating an example of an operating lever.

ON and OFF of the first cutoff circuit 90*a* and the second cutoff circuit 90*b* are operated by an operating part 91, such as an operating lever or an operating switch. As the operating part, operating levers or the like are respectively provided at the first cutoff circuit 90*a* and the second cutoff circuit 90*b*. However, it is desirable to provide an operating lever capable of simultaneously operating ON and OFF of both the cutoff circuits. FIG. 8 is a view illustrating an example of the operating lever capable of simultaneously operating ON and OFF of the first cutoff circuit 90*a* and the second cutoff circuit 90*b*. In the example illustrated in FIG. 8, the lithium ion battery 61*a* and the lithium ion battery 61*b* are lined up and housed within a frame body 93, and the operating part 91 consisting of the operating lever is provided at the frame body 93. ON and OFF of the first cutoff circuit 90*a* and the second cutoff circuit 90*b* are simultaneously operated by moving the operating lever in the upward-downward direction.

Additionally, the first cutoff circuit 90*a* and the second cutoff circuit 90*b* also may have a configuration in which these cutoff circuits are automatically turned off in a case where an excessive electric current flows. Well-known circuit configurations can be used as the configuration of the auto cutoff circuit.

Figure 9:
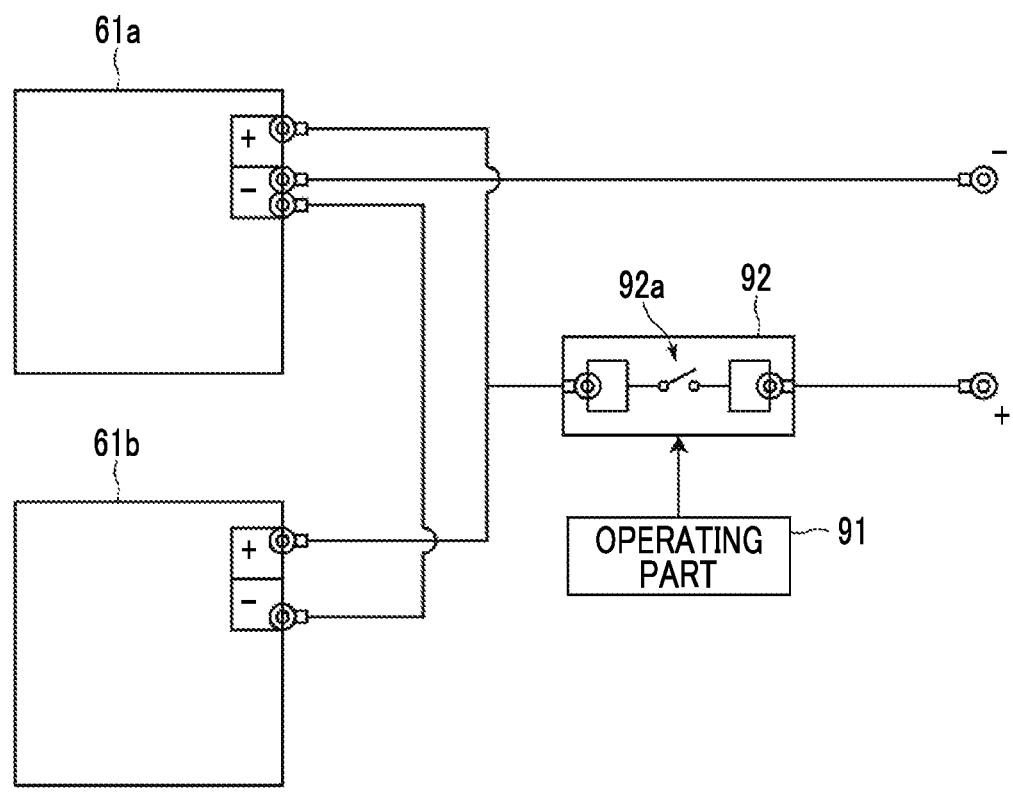
FIG. 9 is a view illustrating another example of the configuration of the cutoff part.

Additionally, the configuration of the cutoff part is not limited to the configuration illustrated in FIG. 7, and a configuration illustrated in FIG. 9 may be adopted. In the configuration of FIG. 9, the positive electrodes of the lithium ion battery 61*a* and the lithium ion battery 61*b* are short-circuited to each other, and the negative electrodes thereof are connected to each other. A cutoff part 92 is connected to a short-circuiting part between the positive electrodes. The cutoff part 92 includes a cutoff circuit 92*a*, and electric power supply from the lithium ion battery 61*a* and the lithium ion battery 61*b* is cut off by turning off the cutoff circuit 92*a*.

For example, in the configuration illustrated in FIG. 7, in a case where the first cutoff circuit 90*a* and the second cutoff circuit 90*b* are brought into an OFF state for a long time, a voltage difference between the two lithium ion batteries 61*a*, 61*b* becomes large. As a result, when the two first and second cutoff circuits 90*a*, 90*b* are turned on, a short-circuit current may flow between the two lithium ion batteries 61*a*, 61*b*, and may have a bad influence on the lithium ion batteries 61*a*, 61*b*. In contrast, according to the configuration of FIG. 9, the positive electrodes and the negative electrodes of the lithium ion battery 61*a* and the lithium ion battery 61*b* are short-circuited to each other, respectively. Thus, the electric potentials of the two lithium ion batteries 61*a*, 61*b* are always in the same state, and the above-described short-circuit current also does not flow.

In addition, ON and OFF of the cutoff circuit 92*a* that are illustrated in FIG. 9 are also operated by the operating part 91, such as an operating lever or an operating switch. The cutoff circuit 92*a* may have a configuration in which this cutoff circuit is automatically turned off in a case where an excessive electric current flows.

In addition, the radiation irradiation device of the invention does not necessarily include the leg part 10 as in the radiation irradiation device 1 of the above embodiment. Additionally, the configuration of the supporting member 30 and the arm part 40 is not limited to the configuration of the above embodiment, and other configurations may be adopted.

EXPLANATION OF REFERENCES

- 1: radiation irradiation device
- 2: device placement surface
- 3: bed
- 10: leg part
- 10*a*: first caster
- 10*b*: second caster
- 11: pedestal part
- 12: foot arm part
- 12*a*: tip part
- 13: pedal part
- 13*a*: first pedal
- 13*b*: second pedal
- 20: main body part
- 21: housing
- 21*a*: flat surface
- 22: control part
- 23: monitor
- 24: input part
- 25: cradle
- 25*a*: insertion port
- 25*b*: connector
- 26: handle part
- 30: supporting member
- 31: rotational movement part
- 32: radiation source attachment part
- 40: arm part
- 50: radiation generating part
- 51: housing
- 52: X-ray tube
- 53: first booster circuit part
- 53*a*: positive electrode side first booster circuit
- 53*b*: negative electrode side first booster circuit
- 54: voltage doubler rectifier circuit part
- 54*a*: positive electrode side voltage doubler rectifier circuit
- 54*b*: negative electrode side voltage doubler rectifier circuit
- 60: electric power supply part
- 61: battery part
- 61*a*, 61*b*: lithium ion battery
- 62: inverter circuit part
- 62*a*: positive electrode side inverter circuit
- 62*b*: negative electrode side inverter circuit
- 63: booster circuit part
- 63*a*: positive electrode side first booster circuit
- 63*b*: negative electrode side second booster circuit
- 70: cable part
- 70*a*: positive electrode side electric power supply wiring line
- 70*b*: negative electrode side electric power supply wiring line
- 80: radiation detector
- 81: detecting part
- 82: housing
- 83: transmission plate
- 85: connector
- 90: cutoff part
- 90*a*, 90*b*: cutoff circuit
- 91: operating part
- 93: frame body
- 92: cutoff part
- 92*a*: cutoff circuit
- AX1, AX2: rotational movement axis
- H: subject
- 84A to 84D: marker

What is claimed is:

1. A radiation irradiation device comprising:
   a radiation generating part that generates radiation;
   an arm part having the radiation generating part attached to one end thereof,
   a main body part having the other end of the arm part connected thereto,
   an electric power supply part provided at the main body part, and
   a cable part for electrically connecting the power supply part and the radiation generating part, wherein the electric power supply part has a battery part having lithium ion batteries connected in parallel, and a first booster circuit part that boosts a voltage output from the battery part, and
   wherein the radiation generating part has a second booster circuit part that further boosts a voltage that is boosted by the first booster circuit part and is input to the radiation generating part via the cable which is extended along the arm part.

2. The radiation irradiation device according to claim 1, wherein the first booster circuit part boosts the voltage output from the battery part to a voltage of 4 times or more and 6 times or less.

3. The radiation irradiation device according to claim 2, wherein the second booster circuit part boosts the voltage input via the arm part to a voltage of 50 times or more.

4. The radiation irradiation device according to claim 3, wherein the same poles of the lithium ion batteries are short-circuited to each other.

5. The radiation irradiation device according to claim 3, further comprising:
   a cutoff part that cuts off electric power supply from the battery part to the radiation generating part.

6. The radiation irradiation device according to claim 2, wherein the same poles of the lithium ion batteries are short-circuited to each other.

7. The radiation irradiation device according to claim 2, further comprising:
   a cutoff part that cuts off electric power supply from the battery part to the radiation generating part.

8. The radiation irradiation device according to claim 1, wherein the second booster circuit part boosts the voltage input via the arm part to a voltage of 50 times or more.

9. The radiation irradiation device according to claim 8, wherein the same poles of the lithium ion batteries are short-circuited to each other.

10. The radiation irradiation device according to claim 8, further comprising:

a cutoff part that cuts off electric power supply from the battery part to the radiation generating part.

11. The radiation irradiation device according to claim 1, wherein a voltage output from the first booster circuit part is 60 V or more and 300 V or less.

12. The radiation irradiation device according to claim 11, wherein the same poles of the lithium ion batteries are short-circuited to each other.

13. The radiation irradiation device according to claim 1, wherein the same poles of the lithium ion batteries are short-circuited to each other.

14. The radiation irradiation device according to claim 1, further comprising:
a cutoff part that cuts off electric power supply from the battery part to the radiation generating part.

15. The radiation irradiation device according to claim 14, wherein the cutoff part has a cutoff circuit provided in each of the lithium ion batteries of the battery part.

16. The radiation irradiation device of claim 15, further comprising:
an operating part capable of simultaneously operating a plurality of the cutoff circuits.

17. The radiation irradiation device according to claim 14, wherein the same poles of the lithium ion batteries are short-circuited to each other, and the cutoff part is provided in the short-circuited part.

18. The radiation irradiation device according to claim 1, wherein the voltage output from the battery part is 60 V or less.

19. The radiation irradiation device according to claim 1, wherein the battery part is capable of charging a radiation detector that detects the radiation transmitted through a subject.

20. The radiation irradiation device according to claim 1, wherein the battery part is capable of supplying electric power to an external instrument.

\* \* \* \* \*